United States Patent [19]

DeLuca et al.

[11] Patent Number: 4,769,181
[45] Date of Patent: Sep. 6, 1988

[54] 1,25-DIHYDROXYVITAMIN $D_2$ COMPOUNDS

[75] Inventors: Hector F. DeLuca; Heinrich K. Schnoes; Rafal R. Sicinski; Yoko Tanaka, all of Madison, Wis.

[73] Assignee: Wisconsin Alumni Research Foundation, Madison, Wis.

[21] Appl. No.: 549,047

[22] Filed: Nov. 7, 1983

[51] Int. Cl.$^4$ ................................................ C07J 9/00
[52] U.S. Cl. ................................................ 260/397.2
[58] Field of Search ...................... 260/397.2; 424/236

[56] References Cited

U.S. PATENT DOCUMENTS 4,225,596 9/1980 DeLuca ........................... 260/397.2
4,260,549 4/1981 DeLuca et al. ................. 260/397.2

Primary Examiner—Leonard Schenkman
Assistant Examiner—Joseph A. Lipovsky
Attorney, Agent, or Firm—Howard W. Bremer

[57] ABSTRACT

The invention is directed to the preparation of hydroxylated compounds of the vitamin $D_2$ series and specifically to a process for synthesizing $1\alpha,25$-dihydroxyvitamin $D_2$, $1\beta,25$-dihydroxyvitamin $D_2$, their corresponding 5,6-trans isomers and the C-24 epimers of these compounds.

The hydroxylated vitamin $D_2$ compounds obtained exhibit vitamin D-like activity and can be substituted for vitamin $D_3$ or various of its known metabolites where such compounds are applied.

1 Claim, No Drawings

1,25-DIHYDROXYVITAMIN D₂ COMPOUNDS

This invention was made with Government support under NIH Grant No. AM 14881 awarded by the Department of Health and Human Services. The Government has certain rights in this invention.

TECHNICAL FIELD

This invention relates to the preparation of hydroxylated compounds of the vitamin $D_2$ series.

More specifically, this invention relates to a process for the synthesis of $1\alpha,25$-dihydroxyvitamin $D_2$ and $1\beta,25$-dihydroxyvitamin $D_2$, of the corresponding 5,6-trans-isomers, and the C-24 epimers of these compounds.

BACKGROUND ART

The importance of hydroxylated forms of vitamin D as regulators of calcium and phosphate metabolism in animals and humans is by now well established through many disclosures in the patent and general literature. Vitamin $D_3$, the natural form of the vitamin produced in skin, is known to be hydroxylated in vivo to 25-hydroxyvitamin $D_3$ and then to $1\alpha,25$-dihydroxyvitamin $D_3$, the latter compound being generally regarded as the tissue-active hormonal form of the vitamin. Likewise, vitamin $D_2$, which is commonly used as a food additive or vitamin D supplement, undergoes the same hydroxylation sequence in vivo to form 25-hydroxyvitamin $D_2$ (25-OH-$D_2$) and $1\alpha,25$-dihydroxyvitamin $D_2$ ($1\alpha,25$-(OH)$_2$D$_2$), the latter being essentially as active as $1\alpha,25$-dihydroxyvitamin $D_3$ in humans and other mammals.

Both 25-OH-$D_2$ and $1\alpha,25$-(OH)$_2$D$_2$, the structures of which are shown below, have been isolated and characterized as metabolites of vitamin $D_2$ (DeLuca et al., U.S. Pat Nos. 3,585,221; 3,880,894).

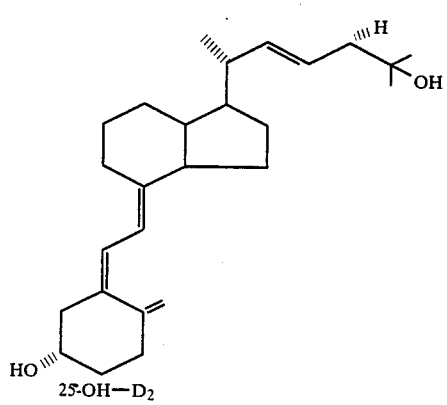

25-OH—D₂

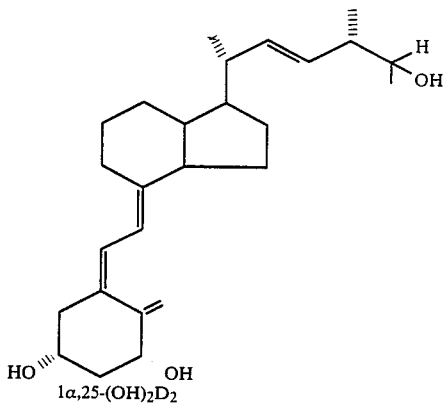

1α,25-(OH)₂D₂

These metabolites, being derived from vitamin $D_2$, are characterized by the S-stereochemistry at carbon 24, as shown above.

DISCLOSURE OF INVENTION

A process for the preparation of 1,25-dihydroxyvitamin $D_2$ compounds has now been developed. The process is notable in that, in addition to the 5,6-cis- and trans-$1\alpha,25$-dihydroxy vitamin $D_2$ compounds, it also provides $1\beta,25$-dihydroxyvitamin $D_2$ compounds and the corresponding 5,6-trans isomers. These latter analogs are of particular interest because of their unexpectedly potent biological properties.

The synthetic process is outlined in Scheme I. Specific compound designations by Arabic numeral or letter (e.g. 1, 2, . . . 6a, 6b, etc.) as used in the following description or the Examples refer to the structures so numbered in Scheme I or in the body of this disclosure. A wavy line drawn to a substituent in these structures, e.g. as in the case of the substituent at carbons 1 and 24, indicates that such substituent may have either of the two possible stereochemical configurations.

BEST MODE FOR CARRYING OUT THE INVENTION

A convenient starting material for this process is 25-hydroxyvitamin $D_2$ (structure 1, 24S-sterochemistry), or its 24R-epimer, 25-hydroxy-24-epi-vitamin $D_2$ (structure 1, 24R-stereochemistry), or a mixture of both compounds.

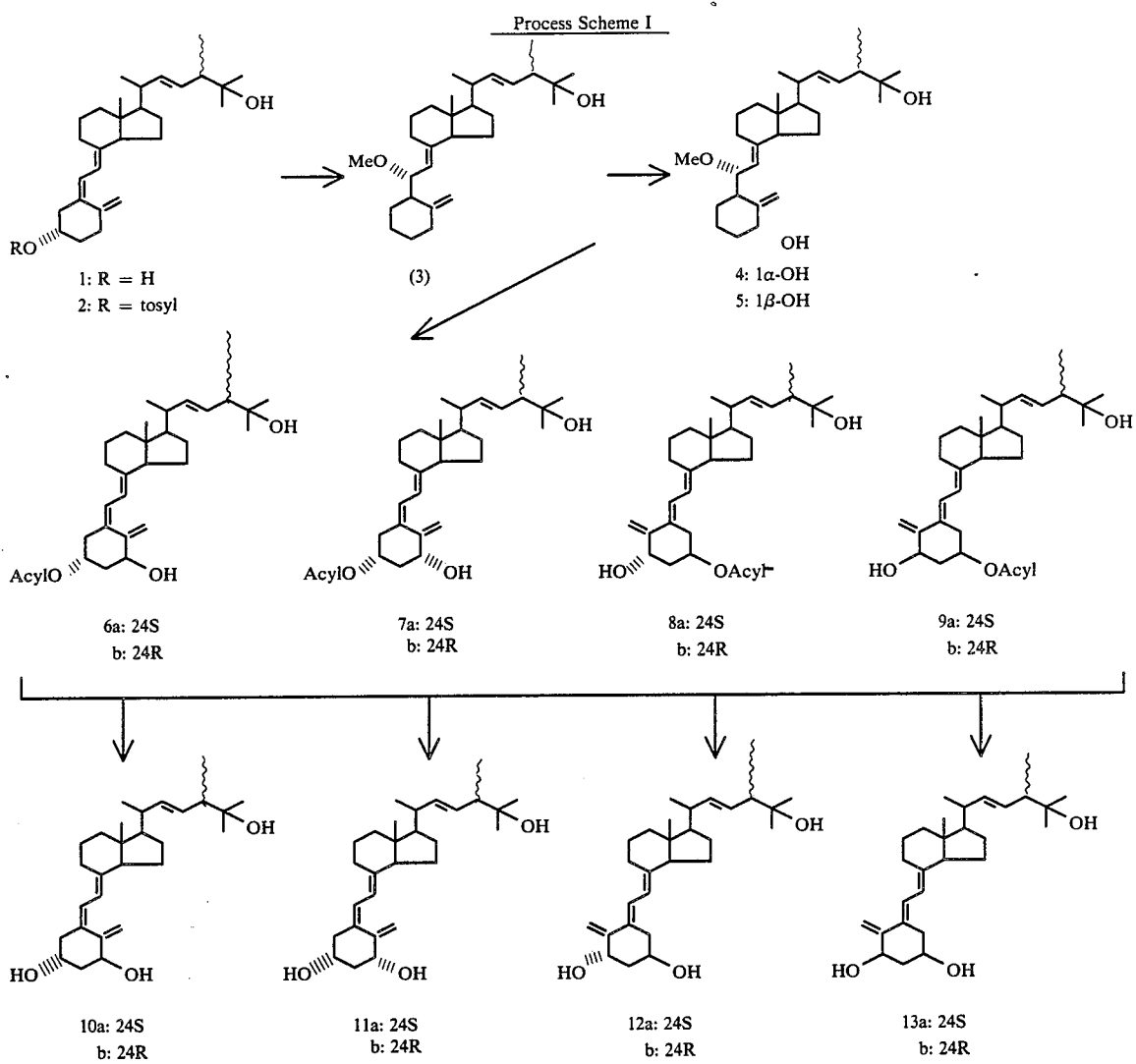

Process Scheme I

Both 25-hydroxyvitamin D₂, having the natural 24S-configuration, and its 24R-epimer ia a known compound. The 24R-epimer has been prepared previously (DeLuca, U.S. Pat. No. 3,585,221 and DeLuca et al. U.S. patent application Ser. No. 420,191, filed Sept. 20, 1982). For the purpose of the present process it is convenient to use a mixture of the 24R and S-epimers as starting material, epimer separation being accomplished at a later stage (as described below). It is important to note, however, that the synthetic process can be executed equally well and in an entirely analogous fashion with the pure 24R or 23S-epimer of compound 1 as starting material, whereby, of course, the use of the 24R-epimer would yield specifically the 24R-epimer of the 1,25-dihydroxyvitamin D₂ product, whereas the use of the 24S-epimer would yield the corresponding 24S-1,25-dihydroxyvitamin D₂ product.

The first step of the process comprises conversion of starting material of structure 1 to the corresponding C-3-tosylate (structure 2) using conventional tosylation procedures, and subsequent solvolysis of the tosylate according to the procedures of DeLuca et al., (U.S. Pat. No. 4,195,027) to obtain the cyclovitamin D derivative of structure 3. This intermediate is then subjected to allylic hydroxylation with SeO₂/t-butyl hydroperoxide, to obtain the 1-hydroxy-cyclovitamin D₂ derivatives. This allylic hydroxylation process yields the 1α-hydroxy-cyclovitamin D product represented by structure 4 as expected, but also, in this case, the corresponding 1β-hydroxy isomer of structure 5. Formation of the 1β-hydroxy-isomer in this reaction was unexpected, since in previous work (U.S. Pat. No. 4,195,027) only the 1α-hydroxy product had been recovered. The 1β-hydroxy compound 5 is the minor component of the product mixture. If desired, isomer separation can be accomplished by conventional methods, e.g. high performance chromatography, but for the purposes of the present process, isomer separation is not required at this stage.

Direct solvolysis of this 1-hydroxy-cyclovitamin D₂ product mixture (compounds 4 and 5) in a medium containing a low-molecular weight organic acid, then provides, in admixture, the desired 5,6-cis- and 5,6-trans-1,25-dihydroxyvitamin D₂ compounds as the 3-O-acylates, namely the compounds of structures 6a/b and the corresponding 5,6-trans-isomers (structure 8a/b) and the 1β-hydroxy-epimers of structures 7a/b as well as their corresponding 5,6-trans-isomers (9a/b). After initial fractionation of this mixture by conventional high performance liquid chromatography, followed by mild base hydrolysis of each fraction (to remove the acyl groups) and subsequent further separation and purification of products by high performance chromatography, it is possible to obtain any or all of the following compounds in isolated form: 1α,25-dihydroxyvitamin $D_2$ (10a), the natural product having the 24S-stereochemistry), the corresponding (24R)-epimer, 1α,25-dihydroxy-24-epivitamin $D_2$ (10b), 5,6-trans-1α,25-dihydroxyvitamin $D_2$ (12a), the corresponding (24R)-epimer (12b), as well as 1β,25-dihydroxyvitamin $D_2$ (11a; 24S-stereochemistry) and its (24R)-epimer, 1β,25-dihydroxy-24-epi-vitamin $D_2$ (compound 11b), and the corresponding 5,6-trans-isomers 13a and 13b.

In the present case, compounds 10a, 10b, 11a, 11b, 12a and 12b were recovered by chromatographic separation of the reaction mixture. The 5,6-trans compounds 13a and 13b can also be isolated from the solvolysis mixture by careful chromatography, but when their abundance in the mixture is low so as to make recovery tedious and time-consuming, it is generally more convenient to obtain them from the cis-isomers 11a and 11b by 5,6-double bond isomerization.

Thus, treatment of the 5,6-cis isomer 11a with iodine, according to the conventional procedure, gave upon chromatographic purification, the 5,6-trans isomer 13a; compound 11b was likewise converted to its trans isomer 13b.

In order to securely establish the C-24 stereochemistry of the novel 1β,25-dihydroxyvitamin $D_2$ compounds, these 1β-isomers were also chemically correlated with the known 1α-hydroxy compounds by the following procedure. Treatment of 1α,25-dihydroxyvitamin $D_2$ (10a) with manganese dioxide, gave the corresponding 1-oxo-25-hydroxyprevitamin $D_2$ compound of structure 14a, shown below:

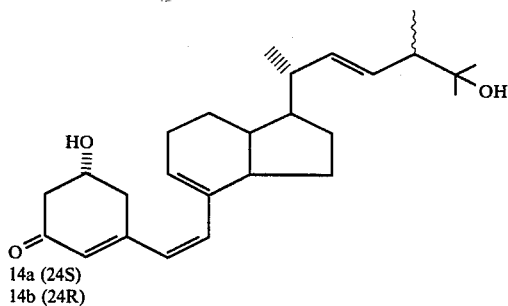

14a (24S)
14b (24R)

Upon reduction of this compound with $LiAlH_4$, and subsequent thermal isomerization of the previtamin chromophore to the vitamin D triene system, there was obtained 1β,25-dihydroxy-vitamin $D_2$ (structure 11a). Like treatment of 1α,25-dihydroxy-24-epivitamin $D_2$ (structure 10b) gave ketone 14b (above) and then 1β,25-dihydroxy-24-epivitamin $D_2$ (structure 11b). These interconversions, and the cis to trans conversions (11a,b to 13a,b) described earlier, relate all four 1β,25-dihydroxyvitamin D compounds with the corresponding 1α-hydroxy-isomers and thus establish the C-24 stereochemistry for all compounds.

Although for therapeutic applications, the free hydroxy compounds represented by structures 10, 11, 12 and 13 are generally used, for some such applications, the corresponding hydroxy-protected derivatives may be useful or preferred. Such hydroxy-protected derivatives are for example the acylated compounds represented by general formulae 15 and 16 below,

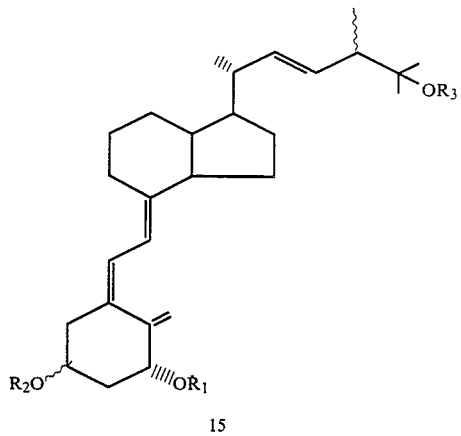

15

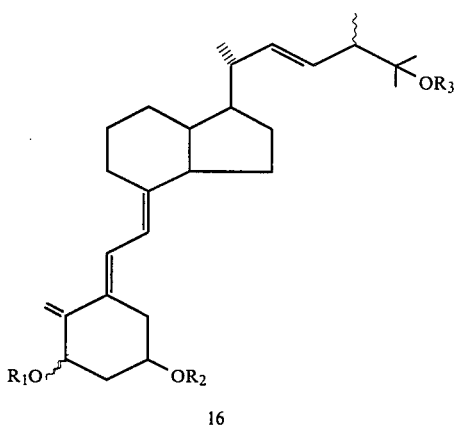

16 wherein each of $R_1$, $R_2$, and $R_3$ is selected from the group onsisting of hydrogen and acyl, except that at least one of $R_1$, $R_2$ and $R_3$ must be acyl. The term 'acyl' refers to an aliphatic acyl group (alkanoyl group) of from 1 to 6 carbons, in all possible isomeric forms (e.g. formyl, acetyl, butyryl, isobutyryl, valeryl, etc.) or an aromatic acyl group (aroyl group), such as benzoyl, or the methyl- halo- or nitro-substituted benzoyl groups, or a dicarboxylic acyl group of from 2 to 6 atoms chain length, i.e. acyl groups of the type $ROOC(CH_2)_nCO—$, or $ROOCCH_2—O—CH_2CO—$, where n has values between 0 and 4 inclusive, and R is hydrogen or an alkyl radical. Representative of such dicarboxylic acyl groups are oxalyl, malonyl, succinoyl, glutaryl, adipyl and diglycolyl. The term 'alkyl' refers to a lower alkyl group of 1 to 6 carbons in all possible isomeric forms, e.g. methyl, ethyl, propyl, isopropyl, isobutyl, pentyl, etc.

Such acyl derivatives are conveniently prepared from the free hydroxy compounds (or, if desired, from the C-3-monoacylated intermediates of structure 6, 7, 8 or 9) by conventional acylation procedures, i.e. treatment of any of the hydroxyvitamin $D_2$ products with an acyl chloride, or acyl anhydride in a suitable solvent such as pyridine, or alkylpyridine. By appropriate selection of reaction time, acylating agent, temperature and solvent, as is well-known in the art, the partially or fully acylated derivatives represented by structures 15 or 16 above are obtained. For example, treatment of 1β,25-dihydroxyvitamin $D_2$ in pyridine solvent with acetic anhydride at room temperature gives the 1,3-diacetate (15, $R_1=R_2=$acetyl, $R_3=H$), while the same reaction conducted at elevated temperature yields the corresponding 1,3,25-triacetate. The 1,3-diacetate can be further acylated at C-25 with a different acyl group; e.g. treatment with benzoyl chloride or succinic anhydride would provide the 1,3-diacetyl-25-benzoyl- or β,3-diacetyl-25-succinoyl-derivative, respectively. A 1,3,25-triacyl derivative can be selectively hydrolyzed in mild base to provide the 1,3-dihydroxy-25-acyl compound, the free hydroxy groups of which can be reacylated, if desired, with different acyl groups. Likewise, a 1,3-diacyl derivative can be subjected to partial acyl hydrolysis to obtain the 1-O-acyl and the 3-O-acyl-compounds, which in turn can be reacylated with different acyl groups. Like treatment of the other hydroxyvitamin $D_2$ products (10, 11, 12 or 13) provides the corresponding desired acyl derivatives of structures 15 or 16.

Like the previously known vitamin $D_2$ metabolite, $1\alpha,25$-dihydroxyvitamin $D_2$ (10a), the novel compounds of this invention exhibit pronounced vitamin D-like activity, and thus represent desirable substitutes for the known vitamin $D_2$ or $D_3$ metabolites in many therapeutic or veterinary applications. Particularly preferred in this regard are the products of structure 13a and 13b. These compounds exhibit high binding affinity for the intestinal receptor protein, and since binding affinity generally correlates with high in vivo activity, these compounds can be expected to be especially useful for the treatment of diseases related to mineral imbalance. The novel compounds may be used for correcting or improving a variety of calcium and phosphate imbalance conditions resulting from a variety of diseases, such as vitamin D-resistant rickets, osteomalacia, hypoparathyroidism, pseudohypoparathyroidism, osteoporosis, Paget's disease, and similar bone and mineral-related disease states well known to the medical practice. The compounds can also be used for the treatment of mineral imbalance conditions in animals, such as the milk fever condition, poultry or swine leg weakness, or for improving egg shell quality of fowl.

For therapeutic purposes, these compounds may be administered orally or by injection or infusion in any form convenient or appropriate to the method of administration selected. Thus the compounds may be formulated with any therapeutically acceptable and innocuous carrier, in the form of pills, tablets or gelatin capsules for oral administration, or they may be formulated as solutions, emulsions, dispersions or suspensions in innocuous solvents and oils, and such formulations may contain also other therapeutically active and beneficial constituents, such as other vitamins, salts, sugars, hormones, etc. as may be appropriate to the specific application. The novel compounds may be administered singly or as mixtures, e.g. mixtures of 13a and 13b, or mixtures of 11a, 11b, 13a, 13b, or any other combination of the individual stereoisomers of this invention. Advantageously, the compounds of this invention are administered in dosage amounts of between about 0.5 to 100 μm per day, it being understood, of course, that the specific dosage administered in any given case will be adjusted in accordance with the specific compound administered, the disease to be treated, the condition of the subject and other relevant medical facts that may modify the activity of the drug or the response of the subject, as is well-known by those skilled in the art.

EXAMPLE 1

Preparation of (24R/S-1,25-dihydroxy-3,5-cyclovitamin $D_2$ (compounds 4 and 5):

Freshly recrystallized p-toluenesulfonly chloride (50 mg) was added to a solution of 33 mg (24R/S)-25-hydroxyvitamin $D_2$ (1) in dry pyridine (300 μl). The reaction mixture was allowed to stand for 30 hours at 4° C., poured into ice/saturated $NaHCO_3$ with stirring and extracted with benzene. The combined extracts were washed with $NaHCO_3$, water, aqueous $CuSO_4$ solution, water, then dried over $MgSO_4$. Removal of solvent under reduced pressure gave a crude tosylate (2), which can be used directly for the next reaction.

A mixture of product (2) and $NaHCO_3$ (150 mg) in 10 ml of anhydrous methanol was heated at 55° C. for 8.5 h with stirring, concentrated to Ca. 2 ml and diluted with 80 ml of benzene. The benzene solution was washed with water, dried over $MgSO_4$ and evaporated. The oily product (3) was sufficiently pure for the following oxidation step.

To a stirred suspension of 4 mg of $SeO_2$ in 5 ml of dry $CH_2Cl_2$ was added 13.2 μl of t-BuOOH. After 0.5 h, 40 μl of anhydrous pyridine was added and the mixture was stirred at room temperature until homogeneous. Dichloromethane (3 ml) was then added, the solution was cooled to 0° C. and the cyclovitamin product (3) was added in 4.5 ml of $CH_2Cl_2$. After 15 min, the reaction was allowed to warm slowly to room temperature and continued until almost all starting material was consumed (Ca. 30 min). The mixture was transferred to a separating funnel and shaken with 30 ml of 10% NaOH. Ether (150 ml) was added and the phases were separated. The etheral phase was washed with 10% NaOH, water, dried over $MgSO_4$ and evaporated in vacuo. The oily residue was purified by preparative TLC (developed with 6:4 n-hexane-ethyl acetate). The isolated product (12 mg) represents a mixture containing $1\alpha$-hydroxyclovitamin 4 and a lesser amount of the corresponding $1\beta$-hydroxy derivative 5, and is characterized by the following physical data: mass spectrum, m/e 442 ($M^+$, 13), 424 (8), 410 (9), 392 (26), 352 (15), 269 (27), 135 (88), 59 (100); NMR ($CDCl_3$) δ 0.55 (3H, s, 18-$H_3$), 0.63 (1H, m, 3-H), 1.00 (3H, d, J=6.5 Hz, 28-$H_3$), 1.05 (3H, d, J=6.5 Hz, 21-$H_3$), 1.13 and 1.18 (6H, each s, 26-$H_3$ and 27-$H_3$), 3.26 (3H, s, 6-$OCH_3$), 4.19 (1H, d, J=9.5 Hz, 6-H), ~4.2 (1H, m, 1-H), 4.96 (1H, d, J=9.5 Hz, 7-H), 5.17 and 5.24 (2H, each m, 19-$H_2$), 5.35 (2H, broad m, 22-H and 23-H).

EXAMPLE 2

(a) Cycloreversion of 1-hydroxycyclovitamins 4 and 5

A solution containing a mixture of 1-hydroxycyclovitamins 4 and 5 (6 mg) in glacial acetic acid (0.5 ml) was heated at 55° C. for 15 min, cooled and poured carefully over ice-saturated $NaHCO_3$. The mixture was extracted with benzene and ether, and the combined extracts were washed with saturated $NaHCO_3$ and water. The residue was chromatographed on a HPLC column (6.2 mm×25 cm Zorbax-Sil) using 3% 2-propanol in hexane as eluent. Chromatography yielded a fraction (1.4 mg) containing $1\alpha,25$-dihydroxyvitamin $D_2$ 3-acetate (6a) and both 24-epimers of the corresponding $1\beta,25$-dihydroxy derivative 7 (peak collected at 90 ml) as well as a fraction (2.5 mg) containing of (24R)-$1\alpha,25$-dihydroxy-vitamin $D_2$ 3-acetate (6b) and both 24-epimers of the 5,6-trans-$1\alpha,25$-dihydroxyvitamin 8 (peak collected at 97 ml; 1:1 ratio at 6b and 8 was established by NMR).

(b) Hydrolysis of $3\beta$-acetoxy group

A solution of the mixture containing 6a and 7 (1.1 mg) as obtained above in 10% methanolic NaOH (1 ml) was heated at 55° C. for 1 hour, then poured into the water and extracted with benzene, ether and methylene chloride. The organic extracts were washed with water, dried, combined and evaporated. HPLC of the residue (10% 2-propanol/hexane, 6.2×25 cm Zorbax-Sil column) afforded a mixture of 24-epimers of $1\beta,25$-dihydroxyvitamin $D_2$ 11 (0.15 mg, peak collected at 52 ml) and a pure $1\alpha,25$-dihydroxyvitamin $D_2$ 10a (0.6 mg, peak collected at 59 ml). Rechromatography of 11 was performed on HPLC (4.6 mm ×25 cm Zorbax-Sil column using 4% 2-propanol in hexane as an eluent). Pure compounds 11a and 11b were collected at 90 and 97 ml.

By analogous treatment of the mixture containing 6b and 8 (2.4 mg) as obtained above with NaOH a mixture of (24R)-$1\alpha,25$-dihydroxyvitamin $D_2$ (10b) and 24-epimers of 5,6-trans-$1\alpha,25$-dihydroxyvitamin 12 (1.7 mg, 1:1 ratio of 10b and 12) was obtained. Separation of the isomers was achieved on HPLC (4.6×25 cm Zorbax-Sil column, 6% 2-propanol/hexane). The chromatographic peaks for (24S)-5,6-trans-$1\alpha,25$-dihydroxyvitamin $D_2$ (12a), (24R)-$1\alpha,25$-dihydroxyvitamin $D_2$ (10b) and (24R)-5,6-trans-$1\alpha,25$-dihydroxyvitamin $D_2$ (12b) were partially overlapped (57 ml, 59 ml and 62 ml respectively) but recycling afforded pure compounds.

(c) Cis to Trans Isomerization

The 5,6-cis form of the 1,25-dihydroxyvitamin D compounds thus obtained can be converted to the trans compounds by treatment with iodine. Thus, treatment of compound 10a in ether with a catalytic amount of iodine (2% of the amount of 10a), while keeping the solution under diffuse daylight for 1 hr, results in cis to trans isomerization, and after HPLC purification (Zorbax-Sil column, 4.6×25 cm), 6% 2-propanol/hexane), the 5,6-trans-isomer 12a was obtained. Under like conditions, compound 10b is isomerized to 12b. Similarly, compound 11a, upon treatment with iodine under the above conditions provided a mixture of the 5,6-cis and 5,6-trans-isomer (11a, 13a) which when separated by HPLC (Zorbax-Sil, 9.6×25 cm, 10% 2-propanol/hexane) gave 13a in pure form, and treatment of compound 11b, under the same conditions, gave the 5,6-trans compound 13b. These cis to trans conversions are useful for correlating the respective C-24-epimers of the major 5,6-cis products with the minor 5,6-trans compounds resulting from the above solvolysis. Also, if the quantity of starting material used in the above solvolysis reaction is low, so as to make purification of the minor trans isomers from the solvolysis mixture inefficient or unduly time consuming, the cis to trans conversion may be used for preparing quantities of pure trans material.

The following spectral data characterize the products obtained:

$1\alpha,25$-dihydroxyvitamin $D_2$ (10a): UV (EtOH) $\lambda_{max}$ 265.5 nm, $\lambda_{min}$ 227.5 nm; mass spectrum, m/e 428 (M+, 6), 410 (4), 352 (4), 287 (6), 269 (10), 251 (10), 152 (42), 134 (100), 59 (99); NMR (CDCl$_3$) δ 0.56 (3H, s, 18-H$_3$), 1.01 (3H, d, J=6.5 Hz, 28-H$_3$), 1.04 (3H, d, J=6.5 Hz, 21-H$_3$), 1.14 and 1.18 (6H, each s, 26-H$_3$ and 27-H$_3$), 4.24 (1H, m, 3-H), 4.43 (1H, m, 1-H), 5.01 (1H, m, 19-H), 5.34 (3H, broad m, 19-H, 22-H and 23-H), 6.02 (1H, d, J=11 Hz, 7-H), 6.39 (1H, d, J=11 Hz, 6-H).

$1\alpha,25$-dihydroxy-24-epivitamin $D_2$ (10b): UV (EtOH) $\lambda_{max}$ 265.5 nm, $\lambda_{min}$ 227.5 nm; mass spectrum, m/e 428 (M+, 13), 410 (9), 352 (7), 287 (11), 269 (15), 251 (13), 152 (52), 134 (100), 59 (97).

$1\beta,25$-dihydroxyvitamin $D_2$ (11a): UV (EtOH) $\lambda_{max}$ 263.5 nm, $\lambda_{min}$ 227 nm; mass spectrum, m/e 428 (M+, 9), 410 (27), 392 (12), 352 (8), 334 (7), 269 (12), 251 (15), 152 (48), 135 (68), 134 (53), 59 (100).

$1\beta,25$-dihydroxy-24-epivitamin $D_2$ (11b): UV (EtOH) $\lambda_{max}$ 263.5 nm, $\lambda_{min}$ 227 nm; mass spectrum, m/e 428 (M+, 10), 410 (29), 392 (13), 352 (9), 334 (7), 269 (13), 251 (16), 152 (58), 135 (76), 134 (59), 59 (100).

5,6-trans-$1\alpha,25$-dihydroxyvitamin $D_2$ (12a): UV (EtOH) $\lambda_{max}$ 273.5 nm, $\lambda_{min}$ 230 nm; mass spectrum, m/e 428 (M+, 8), 410 (3), 287 (3), 269 (7), 251 (7), 152 (34), 134 (100), 59 (78).

5,6-trans-$1\alpha,25$-dihydroxy-24-epivitamin $D_2$ (12b): UV (EtOH) $\lambda_{max}$ 273.5 nm, $\lambda_{min}$ 230 nm; mass spectrum, m/e 428 (M+, 10), 410 (4), 352 (4), 287 (5), 269 (9), 251 (8), 152 (37), 134 (100), 59 (82).

5,6-trans-$1\beta,25$-dihydroxyvitamin $D_2$ (13a): UV (EtOH) $\lambda_{max}$ 270 nm, $\lambda_{min}$ 229.5 nm; mass spectrum, m/e 428 (11), 410 (5), 351 (4), 287 (4), 269 (12), 251 (11), 152 (67), 135 (100), 134 (75), 59 (72).

5,6-trans-$1\beta,25$-dihydroxy-24-epivitamin $D_2$ (13b): UV (EtOH) $\lambda_{max}$ 270 nm, $\lambda_{min}$ 229.5 nm; mass spectrum, m/e 428 (M+, 11), 410 (4), 351 (4), 287 (4), 269 (13), 251 (12), 152 (64), 135 (100), 134 (70), 59 (63).

EXAMPLE 3

Conversion of $1\alpha,25$-dihydroxyvitamins $D_2$ (10a,b) to $1\beta,25$-dihydroxyvitamin $D_2$ analogs (11a,b):

A solution of $1\alpha,25$-dihydroxyvitamin $D_2$ 10a (40 μg) in anhydrous ether (1 ml) was treated with activated MnO$_2$ (6 mg) for 5 h at room temperature. The mixture was filtered (Celite), evaporated and the residue was chromatographed on HPLC column (6.2 mm ×25 cm Zorbax-Sil) using 10% of iPrOH/hexane mixture as an eluent. 1-oxo-previtamin 14a [UV:$\lambda_{max}$ (Et$_2$O) 233.5, 297 nm] was collected at 26 ml. Compound 14a was then reduced with LiALH$_4$ in anhydrous ether (−23° C., 40 min). Excess of reagent was decomposed with water, anhydrous MgSO$_4$ was added and inorganic material was filtered off. After removal of the solvent, the organic residue was dissolved in EtOH and refluxed for 2.5 hours under argon atmosphere. Products were separated by HPLC (9.4 mm×25 cm Zorbax-Sil column) using 15% iPrOH/hexane mixture. Pure $1\beta,25$-dihydroxyvitamin $D_2$ 11a was collected at 55 ml and $1\alpha,25$-dihydroxyvitamin $D_2$ 10a at 63 ml (3:1 ratio of 11a and 10a).

The analogous reaction sequence, performed with $1\alpha,25$-dihydroxy-24-epivitamin $D_2$ (10b) resulted in formation of $1\beta,25$-dihydroxy-24-epivitamin $D_2$ (11b).

The following Example and its accompanying schematic, in each of which like compounds are designated by like numbers, illustrate a method for preparing the starting materials for the process of the present invention.

EXAMPLE 4

The C-22 aldehyde (1) is obtained by degradation of ergosterol acetate (in which the ring B diene system has been protected by Diels-Alder addition of 4-phenyl-1,2,4-triazoline-3,5-dione) according to the procedure of Barton et al. J. Chem. Soc. (c) 1968 (1971). The i-ether aldehyde (4) is obtained from stigmasterol by the method of U.S. Pat. No. 2,623,052.

Synthesis of the Side Chain Fragment (Sulfone A)

To a stirred solution of 4-hydroxy-3-methylbutan-2-one (12.75 g; 0.125 mol) in pyridine (100 ml) is added p-toluenesulfonyl chloride (p-TsCl) (33.25 g, 0.175 mol) in portions, and after standing for 14 hour at room temperature, the reaction mixture is poured into water and extracted with $CH_2Cl_2$. The extract is washed several times with aqueous $CuSO_4$ solution and water and then dried over anhydrous sodium sulfate. Removal of solvent under reduced pressure gives the crude tosylate which is used directly for the next reaction.

Thiphenol (14 g) dissolved in DMF (100 ml) is treated with t-BuOK (14 g). To this reagent, the tosylate is added and after 12 hour at room temperature, the reaction mixture is poured into water and extracted with $CH_2Cl_2$. The extract is washed with aqueous $Na_2CO_3$ solution and water, then dried. Evaporation of solvent gives an oily residue which is purified by silica gel column chromatography. Pure phenyl sulfide is eluted with benzene (yield 15 g).

To this phenyl sulfide derivative (15 g), in benzene (100 ml), ethylene glycol (6 g) and p-TsOH (20 mg) is added and the reaction mixture is heated under a Dean-Stark trap for 3 hour. After cooling, it is extracted with $Na_2CO_3$ solution and water, then dried and the solvent is evaporated. The product, the desired ketal, is chromatographically homogenous and can be used in the next step without further purification.

Crude ketal in dichloromethane (250 ml) solution is treated with m-chloroperbenzoic acid (m-CPBA) (80-85%, 27 g, added in portions) while maintaining the temperature of the reaction mixture below 30° C. After the addition of reagent, the reaction is allowed to stand at room temperature with occasional shaking. When the reaction reaches completion (about 1.5 hour), the aromatic acids are removed by extraction with aqueous $NH_3$, and the organic layer is washed with water and dried. Evaporation of solvent gives the oily sulfone (sulfone A) in essentially quantitative yield (19 g). The product is substantially pure (homogenous by TLC) and can be used without any further purification; $^1$H-NMR; $\delta$; 1.18 (d, J=7 Hz, 3H, $CH_3$—CH—), 1.19 (s, 3H, $CH_3$—C—), 3.84 (m, 4H, ketal-H), 7.3-7.6 and 7.6-7.9 (m, 3H+2H, aromatic protons); IR, $\gamma_{max}^{KBr}$: 1305, 1147, 1082 $cm^{-1}$; mass spectrum, m/z (rel. intensity): 255 (M+-Me, 21), 184 (66), 87 (92), 43 (100).

Coupling of Sulfone A to Aldehyde (1): Hydroxysulfone (2) and Olefin (3).

Grignard reagent is prepared from Mg (535 mg; 22.22 mmol) and ethyl bromide in ether (10 ml), and the virorously stirred solution is treated with sulfone A (6 g; 2.22 mmol) in benzene (6 ml). The precipitate formed is ground with a spatula, stirring is continued, and after 15 min the aldehyde (1) (2.0 g) is added in benzene (10 ml). The reaction mixture is stirred at room temperature for 24 hour, then poured into aqueous $(NH_4)_2SO_4$ solution and extracted with benzene. The organic layer, after washing with water, drying and evaporation gives an oily residue which is chromatographed on silica gel. In the benzene-ether fractions (8:2), excess sulfone is recovered (4.5 g); elution with benzene-ether (3:1) affords unreacted aldehyde (1) (1.0 g); the reaction products (2) are eluted with ethyl acetate.

The crude mixture of steroidal $\alpha$-hydroxysulfones (2) is dissolved in methanol (200 ml) saturated with $Na_2HPO_4$. Sodium amalgam (5.65%, 15 g) is added and the reaction mixture is stirred at 4° C. for 15 hour.

After completion of the Na/Hg reduction, mercury is removed by filtration, and methanol by evaporation under reduced pressure, water is added and the organic material is extracted with benzene. After drying and evaporation of solvent, the oily residue is chromatographed on a silica gel column. Elution with benzene-ether (1:4) gives compound (3) a colorless foam; $^1$H-NMR, $\delta$: 0.80 (s, 18-H), 0.97 (s, 19-H), 1.22 (s, 26-H), 3.93 (m, 4H, ketal-H), 4.44 (m, 1H, 3-H), 5.25-5.45 (m, 2H, 22-H and 23-H), 6.23 and 6.39 (doublets, J=8 Hz, 2×1H, 7-H and 6-H), 7.25-7.45 (m, 5H, —$C_6H_5$); IR, $\gamma_{max}^{CHCl_3}$: 3603 (O—H), 1749, 1692 (C=O), 1406, 1038 $cm^{-1}$; mass spectrum, m/z: 440 (M+-triazoline, 24), 87 (100).

(To increase yield, unreacted aldehyde (1), as recovered above, can be recycled through the sulfone addition, and the resulting $\alpha$-hydroxy sulfones (2) are then, as above, treated with sodium amalgam in buffered methanol to provide additional olefin (3). The above reactions are preferably conducted under an inert atmosphere, such as argon.)

Coupling of Sulfone A to Aldehyde (4): Hydroxysulfone (5) and Olefin (6).

Grignard reagent is prepared from Mg (75 mg, 3.1 mmol) and ethyl bromide in ether (10 ml). To the stirred solution of ethyl magnesium bromide, sulfone A (891 mg; 3.3 mmol) in benzene (5 ml) is added. After stirring the resulting suspension at room temperature for 15 min, a solution of aldehyde (4) (290 mg) in benzene (5 ml) is added. The reaction is continued for 2.5 h, then quenched with saturated $(NH_4)_2SO_4$ solution (5 ml) and diluted with ether. The separated organic layer is washed with water, dried, and evaporated. The oily residue containing (5) is treated with acetic anhydride (2 ml) and pyridine (2 ml). The reaction mixture is allowed to stand for 24 hours, poured into water and extracted with benzene. The benzene extract is washed with an aqueous solution of $CuSO_4$, water, dried, and evaporated. The crude product [the acetate of (5)] is dissolved in methanol saturated with $Na_2HPO_4$ and sodium amalgam (5.65%, 8 g) is added. The reaction mixture is stirred at 4° C. for 16 hours. After the reaction, mercury is removed by filtration, methanol is evaporated, and water and benzene are added to dissolve the residue. The benzene layer is dried and evaporated. The oily residue is chromatographed over silica gel. Elution with benzene-ether mixture (93:7) affords compound (6) (206 mg; 54%), $^1$H-NMR, $\delta$: 0.74 (s, 18-H), 1.04 (s, 19-H), 1.25 (s, 26-H), 2.78 (m, 1H, 6—H), 3.34 (s, 3H, —$OCH_3$), 3.97 (m, 4H, ketal-H), 5.25-5.45 (m, 2H, 22-H and 23-H), IR, $\gamma_{max}^{KBr}$: 3470 (O—H), 1095 $cm^{-1}$; mass spectrum, m/z (rel. intensity): 456 (M+, 1), 441 (M+-Me, 45), 87 (100). It should be noted that the acetylation step described above is not essential and may be omitted if desired; i.e. the hydroxysulfone (5) may be submitted directly to Na/Hg-reduction, as in Example 3. The above reactions are preferably conducted under an inert atmosphere, e.g. argon.

Removal of PTAD-protecting Group: 5,7-Diene (7).

A mixture of the compound (3) (1 g) and lithium aluminum hydride (1.8 g) in THF (120 ml) is heated under reflux for 10 hours. After cooling, excess reagent is destroyed with a few drops of water, and the mixture is dried over anhydrous $MgSO_4$, filtered, and solvent is evaporated to give colorless crystalline material. Crude diene 7 is repeatedly crystallized from ethanol; first and second crops combined give 415 mg of (7). The mother liquor is chromatographed on silica gel column, to give with benzene-ether (7:3), an additional 120 mg of (7); total yield 535 mg (79%); m.p. 132°-134° C. (from ethanol), $^1$H-NMR, $\delta$: 0.63 (s, 18-H), 0.95 (s, 19-H), 1.23 (s, 26-H), 3.63 (m, 1H, 3-H), 3.95 (m, 4H, ketal-H), 5.20-5.50 (m, 3H, 22-H, 23-H and 7-H), 5.57 (m, 1H, 6-H); IR, $\gamma_{max}^{KBr}$: 3430 (O-H), 1063, 1038 $cm^{-1}$; mass spectrum, m/z (rel. int.): 440 (M+, 50), 407 (M+-

$H_2O$—Me, 11), 87 (100); UV, $\lambda_{max}^{EtOH}$: 282 nm ($\epsilon=11,000$).

Irradiation of Compound (7): Previtamin Analog (8).

A solution of diene (7) (50 mg) in 150 ml of benzene-ether (1:4) is cooled on ice and deoxygenated with argon for 20 min. The reaction mixture is irradiated under argon atmosphere for 18 min with a mercury arc lamp (Hanovia SA-1) fitted with a Vycor filter. The solvent is evaporated and the residue is chromatographed on HPLC (6.2 mm×25 cm microparticulate silica gel, 4 ml/min, 1400 psi) and eluted with 2% 2-propanol in hexane to yield 22 mg (44%) of previtamin (8); $^1$H-NMR; δ: 0.73 (s, 18-$\underline{H}$), 1.24 (s, 26-$\underline{H}$), 1.64 (s, 19-$\underline{H}$), 3.96 (m, 5H, ketal-$\underline{H}$ and 3-$\underline{H}$), 5.35 (m, 2H, 22-$\underline{H}$ and 23-$\underline{H}$), 5.50 (m, 1H, 9-$\underline{H}$), 5.69 and 5.94 (doublets, J=11.5 Hz, 2×1H, 6-$\underline{H}$ and 7-$\underline{H}$); UV, $\lambda_{max}^{EtOH}$: 263 nm ($\epsilon=8,900$).

Isomerization of (8) to the Vitamin-Analog (9).

Previtamin 8 (22 mg) is dissolved in ethanol (40 ml) and heated under reflux for 150 min (argon atmosphere). The product is purified by HPLC to yield 18 mg (82%) of the pure vitamin (9); $^1$H-NMR, δ: 0.75 (s, 18-$\underline{H}$), 1.24 (s, 26-$\underline{H}$), 3.94 (m, 5H, ketal-$\underline{H}$ and 3-$\underline{H}$), 4.81 and 5.04 (2 narrow m, 2×1H, 19(Z)- and 19(E)-$\underline{H}$, 5.33 (m, 2H, 22-$\underline{H}$ and 23-$\underline{H}$), 6.03 (d, J=11 Hz, 1H, 7-$\underline{H}$), 6.22 (d, J=11 Hz, 1H, 6-$\underline{H}$); mass spectrum, m/z (rel. int.): 440 (M+, 17), 87 (100), UV, $\lambda_{max}^{EtOH}$: 265 nm ($\epsilon=17,000$).

Hydrolysis of the ketal: Keto-Vitamin $D_2$-Analog (10).

To the solution of compound (9) (18 mg) in ethanol (35 ml), p-toluenesulfonic acid (7.5 mg) in water (1 ml) is added and the reaction mixture is heated under reflux for 90 min (the reaction course is monitored by HPLC). The solvent is evaporated, the residue is dissolved in benzene and extracted with water. The benzene solution is dried (anhydrous $MgSO_4$), and evaporated to yield product (10) (16 mg; 99%). $^1$H-NMR, δ: 0.57 (s, 18-$\underline{H}$), 1.04 (d, J=7 Hz, 21-$\underline{H}$), 1.13 (d, J=7 Hz, 28-$\underline{H}$), 2.12 (s, 3H, 26-$\underline{H}$), 3.10 (m, 1H, 24-$\underline{H}$), 3.96 (m, 1H, 3-$\underline{H}$), 4.82 and 5.05 (2 narrow m, 2×1H, 19(Z)- and 19(E)-$\underline{H}$), 5.2–5.5 (m, 2H, 22-$\underline{H}$ and 23-$\underline{H}$), 6.03 (d, J=11.5 Hz, 1H, 7-$\underline{H}$), 6.22 (d, J=11.5 Hz, 1H, 6-$\underline{H}$), IR, $\gamma_{max}^{CHCl_3}$: 3596 (O—H), 1709 cm$^{-1}$ (C=O); mass spectrum, m/z (rel. int.): 396 (M+, 41), 363 (M+-$H_2O$-Me, 13), 271 (M+-side chain, 16), 253 (m+-side chain-$H_2O$, 23), 136 (100), 118 (95); UV, $\lambda_{max}^{EtOH}$: 265 nm ($\epsilon=17,900$).

Reaction of Ketone (10) with Methylmagnesium Iodide: 25-OH-$D_2$, (11a), and its Epimer (11b).

Grignard reagent is prepared from magnesium (240 mg) and methyl iodide in anhydrous ether (20 ml). To one-tenth of this solution (2 ml; 0.5M solution of $CH_3MgI$) ketone (10) (16 mg; 0.04 mmol) in ether (2 ml) is added. The reaction mixture is stirred at room temperature for 2 hours under an inert atmosphere, then quenched with aqueous solution of $NH_4Cl$, diluted with benzene and washed with water. The organic layer is separated, dried and evaporated. The crude product is first purified by silica gel column chromatography (elution with 20% ether in benzene) and the mixture of (11a) and (11b) (16 mg; 96%) thereby obtained is then repeatedly chromatographed on HPLC column using 2% 2-propanol in hexane as an eluent to separate the 24-stereoisomers, 24-epi-25-OH-$D_2$ (11b) and 25-OH-$D_2$ (11a). Chromatography and rechromatography of each stereoisomer yields 4 mg of (11b) (collected at 68 ml), 4 mg of (11a) (collected at 74 ml) and 7 mg of the mixture of both epimers. Treatment of 2 mg of the epimer mixture with excess acetic anhydride in pyridine solution at room temperature overnight followed by standard work-up yields the corresponding 3-O-acetates.

25-OH-$D_2$ (11a): $[\alpha]_D^{25}+56.8°$ (C=0.2 in EtOH); $^1$H-NMR, δ: 0.57 (s, 18-$\underline{H}$), 1.00 (d, J=7 Hz, 28-$\underline{H}$), 1.04 (d, J=7 Hz, 21-$\underline{H}$), 1.15 and 1.17 (2 singlets, 26-$\underline{H}$ and 27-$\underline{H}$), 3.95 (m, 1H, 3-$\underline{H}$), 4.82 and 5.05 (2 narrow m, 2×1H, 19(Z)- and 19(E)-$\underline{H}$), 5.23–5.43 (m, 2H, 22-$\underline{H}$ and 23-$\underline{H}$), 6.05 and 6.22 (2 doublets, J=11 Hz, 2×1H, 7-$\underline{H}$ and 6-$\underline{H}$); IR, $\gamma_{max}^{KBr}$: 3401 (O—H), 1645, 1631 (C=C), 971 cm$^{-1}$ (trans C=C); mass spectrum, m/z (rel. int.): 412 (M+, 63), 394 (M+-$H_2O$, 10), 379 (M+-$H_2O$-Me, 23), 271 (M+-side chain, 37), 253 (M+-side chain-$H_2O$, 43), 136 (100), 118 (86), 59 (99), UV, $\lambda_{max}^{EtOH}$: 265 nm ($\epsilon=17,950$).

24-epi-25-OH-$D_2$ (11b): $[\alpha]_D^{25}+50.7°$ (C=0.2 in EtOH), $^1$H-NMR, δ: 0.57 (s, 18-$\underline{H}$), 0.99 (d, J=Hz, 28-$\underline{H}$), 1.03 (d, J=7 Hz, 21-$\underline{H}$), 1.14 and 1.16 (2 singlets, 26-$\underline{H}$ and 27-$\underline{H}$), 3.94 (m, 1H, 3-$\underline{H}$), 4.82 and 5.03 (2 narrow m, 2×1H, 19(Z) and 19(E)-$\underline{H}$), 5.20–5.40 (m, 2H, 22-$\underline{H}$ and 23-$\underline{H}$), 6.04 and 6.22 (2 doublets, J=11 Hz, 2×1H, 7-$\underline{H}$ and 6-$\underline{H}$), IR, $\gamma_{max}^{KBr}$: 3401 (OH), 1643, 1630 (C=C), 971 cm$^{-1}$ (trans C=C); mass spectrum, m/z (rel. int.): 412 (M+, 62) 394 (M+-$H_2O$; 12), 379 (M+-$H_2O$-Me, 31), 271 (M+-side chain, 44), 253 (M+-side chain-$H_2O$, 55), 136 (100), 118 (67), 59 (38); UV, $\gamma_{max}^{EtOH}$: 265 nm ($\epsilon=17,300$).

It should be noted that from pure provitamin (7) further synthesis (i.e. the irradiation, isomerization, deketalization and Grignard reaction steps) may be accomplished without chromatographic purification of any intermediate. Careful column chromatography on silica gel before the final separation on HPLC removes all by-products.

4,769,181
Scheme for Preparing Starting Compounds
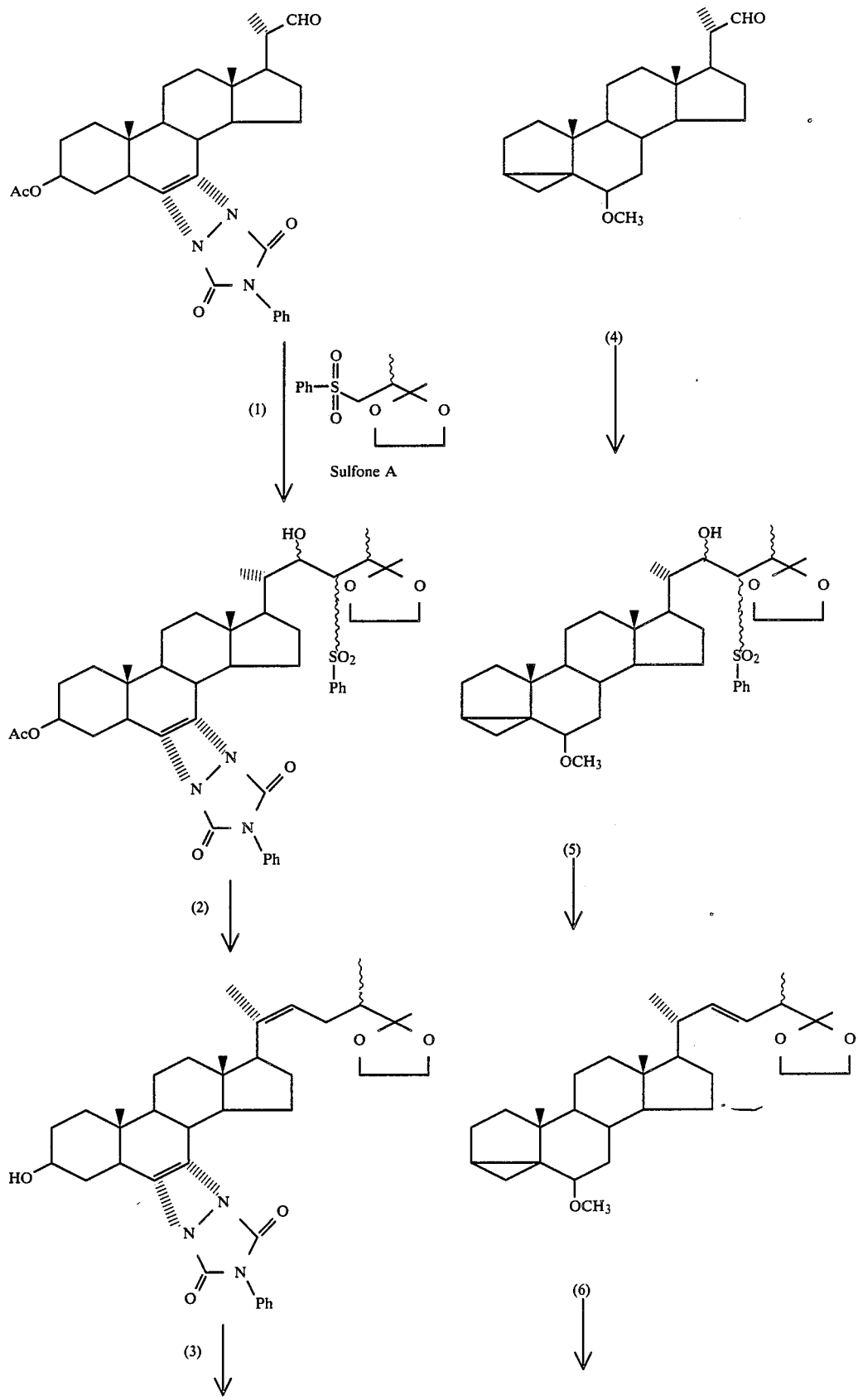

-continued
Scheme for Preparing Starting Compounds
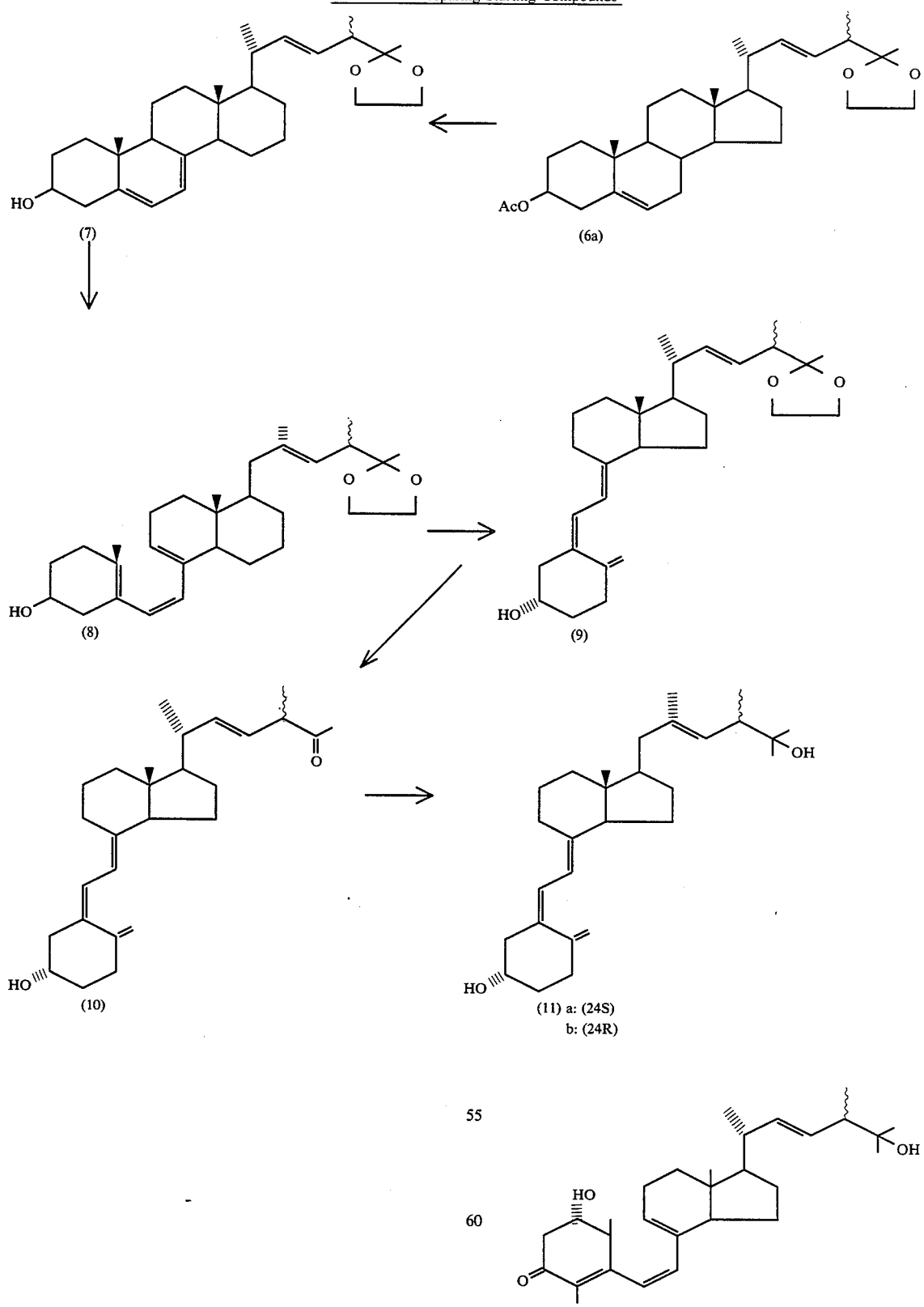
where the methyl group at carbon 24 may have the R or S configuration.
We claim:
1. A compound having the formula:
* * * * *

UNITED STATES PATENT AND TRADEMARK OFFICE
CERTIFICATE OF CORRECTION

PATENT NO. : 4,769,181

DATED : Sep. 6, 1988

INVENTOR(S) : DeLuca, Schnoes, Sicinski, Tanaka

It is certified that error appears in the above-identified patent and that said Letters Patent is hereby corrected as shown below:

In Column 1, at line 55 the structural formula,

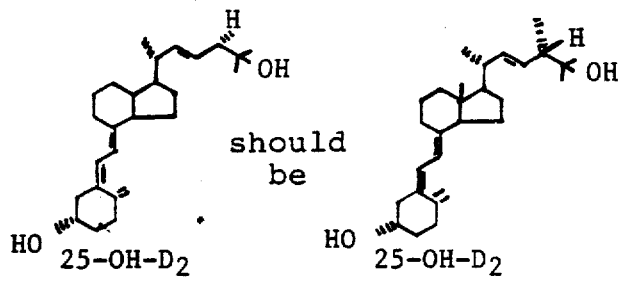

In Column 2, at line 5 the structural formula,

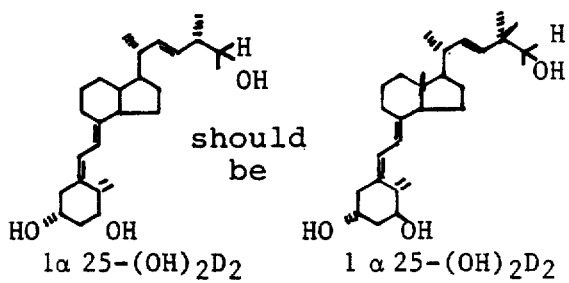

In Column 3, at Process Scheme I, number (3)

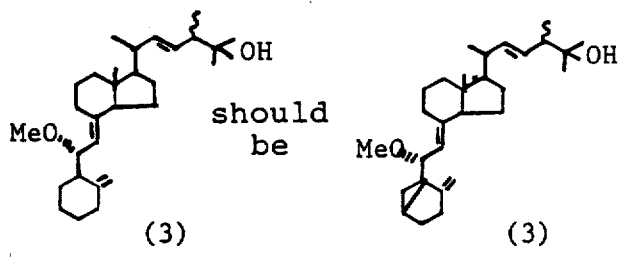

In Column 4, at Process Scheme I, numbers 4:, and 5:

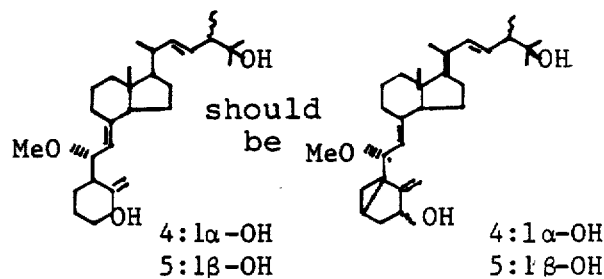

UNITED STATES PATENT AND TRADEMARK OFFICE
CERTIFICATE OF CORRECTION

PATENT NO. : 4,769,181
DATED : Sep. 6, 1988
INVENTOR(S) : DeLuca, Schnoes, Sicinski, Tanaka It is certified that error appears in the above-identified patent and that said Letters Patent is hereby corrected as shown below:

In Column 5, 14a and 14b the structural formula,

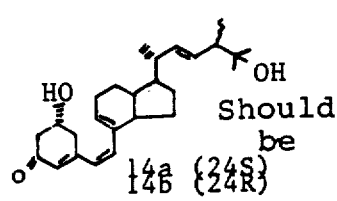 Should be 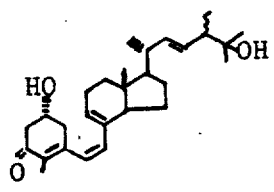

14a (24S)
14b (24R)

In Column 6, 15, the structural formula,

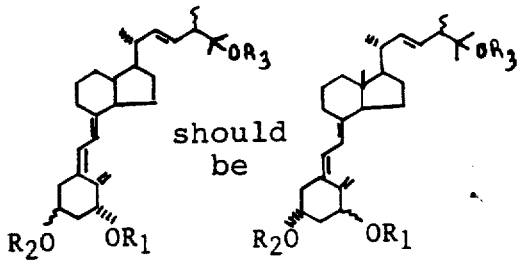 should be 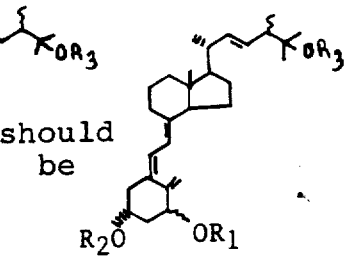

15  15

In Column 6, 16, the structural formula

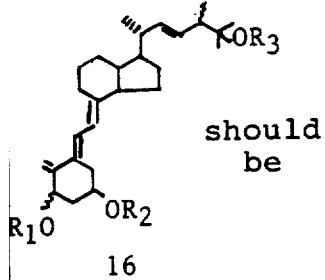 should be 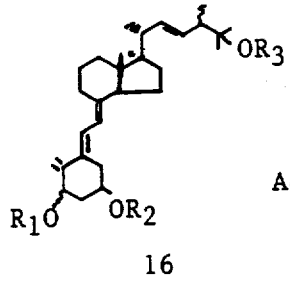

16  16

In Column 15, Scheme for Preparing Starting Compounds number (1)

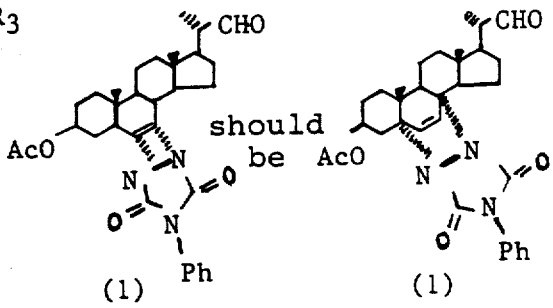 should be 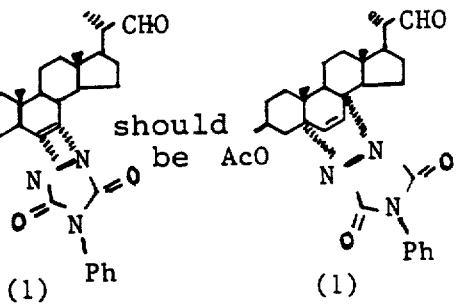

(1)  (1)

UNITED STATES PATENT AND TRADEMARK OFFICE
CERTIFICATE OF CORRECTION

PATENT NO. : 4,769,181
DATED : Sep. 6, 1988
INVENTOR(S) : DeLuca, Schnoes, Sicinski, Tanaka It is certified that error appears in the above-identified patent and that said Letters Patent is hereby corrected as shown below:

In Column 15, number (2), Scheme for Preparing Starting Compounds

In Column 15, number (3), Scheme for Preparing Starting Compounds

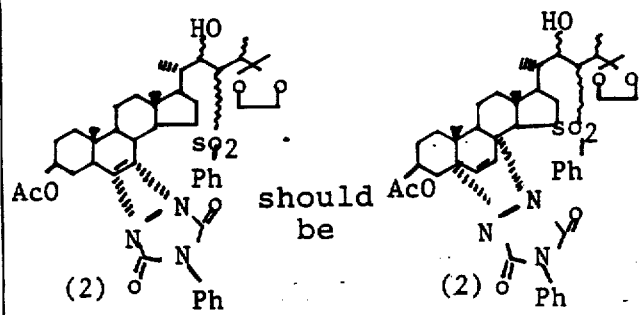

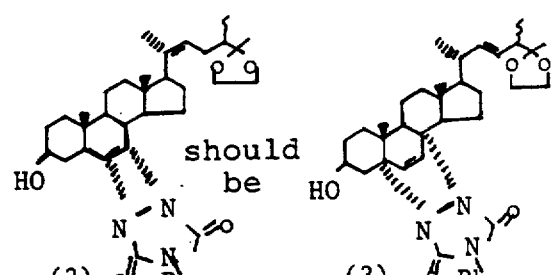

In Column 17, number (8), Scheme for Preparing Starting Compounds

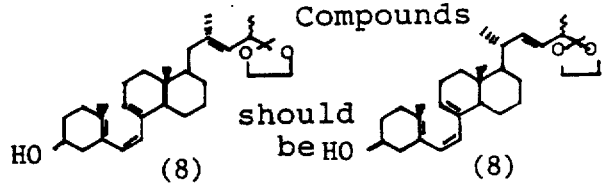

UNITED STATES PATENT AND TRADEMARK OFFICE
CERTIFICATE OF CORRECTION

PATENT NO.  : 4,769,181
DATED       : Sep. 6, 1988
INVENTOR(S) : DeLuca, Schnoes, Sicinski, Tanaka It is certified that error appears in the above-identified patent and that said Letters Patent is hereby corrected as shown below:

In Column 18, number (11)a:,
Scheme for Preparing Starting
Compounds

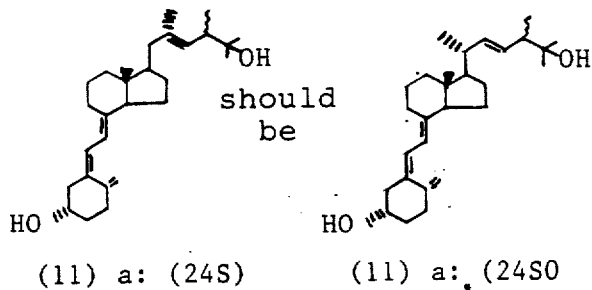

(11) a: (24S)     should be     (11) a: (24SO

Signed and Sealed this

Nineteenth Day of December, 1989

*Attest:*

JEFFREY M. SAMUELS

*Attesting Officer*     *Acting Commissioner of Patents and Trademarks*